(12) United States Patent
Ruddle

(10) Patent No.: US 6,981,869 B2
(45) Date of Patent: Jan. 3, 2006

(54) INJECTION MOLDED ENDODONTIC BRUSH

(76) Inventor: Clifford J. Ruddle, 227 Las Alturas Rd., Santa Barbara, CA (US) 93103

( * ) Notice: Subject to any disclaimer, the term of this patent is extended or adjusted under 35 U.S.C. 154(b) by 0 days.

(21) Appl. No.: 10/420,302

(22) Filed: Apr. 22, 2003

(65) Prior Publication Data

US 2004/0214135 A1 Oct. 28, 2004

(51) Int. Cl.
*A61C 17/02* (2006.01)

(52) U.S. Cl. .................. 433/102; 433/81; 433/224

(58) Field of Classification Search .......... 433/80, 433/81, 102, 119, 224
See application file for complete search history.

(56) References Cited

U.S. PATENT DOCUMENTS

| | | | | |
|---|---|---|---|---|
| 717,594 | A | | 1/1903 | Miles, Jr. |
| 4,280,518 | A | * | 7/1981 | Gambaro .................. 132/323 |
| 4,832,061 | A | * | 5/1989 | Hwang ..................... 132/329 |
| 5,775,346 | A | * | 7/1998 | Szyszkowski ............. 132/329 |
| 5,899,693 | A | | 5/1999 | Himeno et al. |
| 6,059,570 | A | * | 5/2000 | Dragan et al. ............... 433/80 |
| 6,082,999 | A | * | 7/2000 | Tcherny et al. .............. 433/80 |
| 6,085,761 | A | * | 7/2000 | Inaba ....................... 132/329 |
| 6,179,617 | B1 | | 1/2001 | Ruddle |
| D441,141 | S | * | 4/2001 | Shalita ...................... D28/65 |
| 6,343,929 | B1 | * | 2/2002 | Fischer ....................... 433/81 |
| 6,491,520 | B1 | * | 12/2002 | Carlsson et al. ............ 433/118 |
| 6,634,051 | B1 | * | 10/2003 | Dragan et al. ............... 15/106 |
| 6,638,067 | B2 | * | 10/2003 | Fischer et al. .............. 433/102 |
| 2002/0172922 | A1 | * | 11/2002 | Mannschedel ............. 433/102 |

FOREIGN PATENT DOCUMENTS

JP 345852 * 12/2002

OTHER PUBLICATIONS

D.M. Keir, DDS; E.S. Senia, DDS, MS, BS, FACD; and S. Montgomery, DDS, FACD—"Effectiveness of a Brush in Removing Postinstrumentation Canal Debris"—Journal of Endodontics—vol. 16, No. 7, Jul. 1990 -pp. 323-327.
Cohen and Burns, Pathways To The Pulp, 8$^{th}$ Ed. (2002), pp. xiii, 261-262.
International Search Report and Written Opinion from Corresponding International App. No. PCT/US04/08042.

* cited by examiner

*Primary Examiner*—Ralph A. Lewis
(74) *Attorney, Agent, or Firm*—Polster, Lieder, Woodruff & Lucchesi, L.C.

(57) ABSTRACT

Unitary, one-piece plastic molded micro-brushes are provided to remove the smear layer that remains in the root canal and access chamber after the pulp, bacteria, and related irritants have been mechanically and chemically removed from the root canal and access chamber using rotary cutting burs, files and various chemical reagents. The brushes include a handle, shaft or shank and a tapered brush section extending from the distal end of the shank. The brush section includes a plurality of bristles extending radially from a core. The bristles of the root canal brush can be formed in a reverse thread pattern. The brush section of the root canal brush has a diameter of between about 0.1 mm and about 0.2 mm at a tip end and a diameter of between about 0.5 mm and 3 mm at a coronal-most end. The brush section of the root canal brush is about 16 mm long, and has a taper of about 2% to about 12%. In the access chamber brush, the core can be formed as to be spherical, football-shaped, or tapered. The brushes are injection molded from an FDA approved resin.

17 Claims, 5 Drawing Sheets

INJECTION MOLDED ENDODONTIC BRUSH

CROSS-REFERENCE TO RELATED APPLICATIONS

Not Applicable.

STATEMENT REGARDING FEDERALLY SPONSORED RESEARCH OR DEVELOPMENT

Not Applicable.

BACKGROUND OF THE INVENTION

This invention relates to microbrushes, and, in particular, to injection molded brushes which are used during an endodontic or root canal procedure to more predictably clean the root canal system prior to obturation.

Following tooth maturation, the dental pulp is harbored within the structural elements of the tooth. Frequently, and for a variety of reasons, the pulp is irreversibly injured, resulting in inflammatory and infectious conditions which often adversely affect the tooth, its supporting structures, and the patient's health. Clinically, as an alternative to extraction, root canal treatment is performed and ideally directed towards the elimination of pulp, bacteria, and related irritants from the root canal system, followed by three-dimensionally filling the root canal space with an inert, biocompatible, dimensionally stable, filling material, such as gutta percha. The obturation procedures will fill not just the main canal, but the fins, webs, cul-de-sacs, lateral canals, and all portals of exit between the root canal system and the tooth's attachment apparatus.

Root canal procedures are common. In 1994 alone, some 40 million root canal procedures were performed in the United States. Central to a successful endodontic treatment has been the use of chemicals to enhance canal debridement during cleaning and shaping procedures to facilitate the preparation and complete cleaning of the root canal system. The chemicals used to enhance canal debridement during cleaning and shaping procedures potentially reach all aspects of the root canal system. The most popular chemicals currently used during canal preparation to actively assist in cleaning include bleach, hydrogen peroxide, and chelating agents. Often, a 2%–5% solution of a clear, pale, greenish-yellow strongly alkaline solution of sodium hypochlorite (NaOCl) is used.

During canal preparation, the sodium hypochlorite solution is liberally irrigated into the root canal space where its solvent action facilitates the digestion and removal of pulp and bacteria and the destruction and removal of viruses, spores, endotoxins and other irritants generated by the microorganisms in the canal system as the solution penetrates into all aspects of the root canal system. However, studies have shown that even the most thorough use of sodium hypochlorite does not remove all the material from the root canals. The walls of a root canal are comprised of dentin which contains millions of dentinal tubules per square millimeter, and the irritants can find their way into the tubules of the root canal systems. Thus, after cleaning and shaping procedures, the root canal is still covered with a film of debris, frequently described in the literature as a "smear layer." This "smear layer" includes dentinal mud and/or organic debris, including the irritants noted above.

The smear layer or film compromises the sealing of the root canal system with gutta percha and root canal sealer. If obturation is incomplete then the root canal space is predisposed to leakage and failure. Post-treatment failures attributable to leakage are common and require endodontic retreatment of the tooth. Thus, for a complete and thorough cleaning, this smear layer or film should be removed. Once the existence of this smear layer was discovered, practitioners began using a weak acid or surfactant, such as 17% EDTA (ethyldiamine-tetraacetic acid), in an effort to remove the smear layer. Typically, the root canal is flushed with EDTA to accomplish this. Some practitioners have been known to use root canal instruments or files to enhance the performance of the EDTA. The files may be manually used or may be mounted in a rotary or vibratory handpiece. Even when files are used, it is difficult to ensure that the file is brought into contact with the complete surface of the root canal, and hence it is difficult to ensure that substantially all of the smear layer has been removed. Additionally, the use of files, especially with a handpiece, leads to iatrogenic events, such as broken instruments, ledges in the wall of the root canal preparation, or even perforation of the root canal system.

In my prior patent, Pat. No. 6,179,617, which is incorporated herein by reference, I disclosed an endodontic brush for use in removing the smear layer. The brush is comprised of a handle, a shank and a brush section extending from the shank. The brush section includes a core with a plurality of bristles extending from the core. The core was made from a pair of twisted wires. While this brush works acceptably, it still has many shortcomings which are due to the fact that the core and shank are made from wire. Each wire from which the core and shank is made is 0.2 mm in diameter, and hence, the core and shank have a diameter of at least 0.4 mm. While the wires are quite thin, once the bristles are added to the core, the brush section has a diameter that is too large to reach to the end of many canals. The wires cannot be made to be thinner because the brush would then become predisposed to breakage during use. Even at the current diameter, the wire shank and core is too flexible. Because of its high flexibility, a practitioner doing an endodontic procedure cannot effectively and purposely brush the sides of the root canal, using the brush in a brushing manner, and hence cannot thoroughly remove the smear layer from the root canal. Additionally, because of the flexibility of the twisted wire core, the brush cannot be driven ultrasonically. The flexibility of the wire core causes too much of the ultrasonic energy to dissipate prior to reaching the bristles of the brush.

Hence, it would be desirable to provide a brush which can reach the ends of the root canal, which is sufficiently flexible to allow the brush to pass around bends in the root canal, and yet which is sufficiently stiff to allow the endodontist to effectively use lateral pressure so the brush can more intimately contact the root canal wall to remove the smear layer.

BRIEF SUMMARY OF THE INVENTION

Briefly stated, a micro-brush is provided which can be used to reach into the root canal to brush and make intimate contact with normal root canal irregularities that exist even after optimal canal preparation procedures. This brushing action facilitates removing the smear layer which remains in the root canal after the pulp and irritants have been mechanically and chemically removed from the root canal using files and sodium hypochlorite. The brush is used in association with an intracanal irrigant such as EDTA, to remove the debris or smear layer or film, from the root canal.

The brush includes a handle, a shaft or shank and a tapered brush section extending from the shank. The brush section includes a plurality of bristles extending radially from a central core. The bristles are made from a material which is sufficiently stiff so that it will have good rubbing action against the root canal wall to remove the smear layer, which is sufficiently pliable so that it can bend and flex to reach the normal irregularities in the root canal wall, and which is sufficiently soft so that the use of the brush will not form gouges or ledges in the root canal wall (i.e., will not substantially change the normal morphology of the root canal system). The bristles can be formed in a helical pattern so that rotation of the brush in the root canal will pull the contents of the smear layer coronally. The brush can be provided with a handle for manual use or the handle can be adapted or modified to be received in a rotary or vibratory (sonic and ultrasonic) handpieces to impart rotational or vibratory motion to the micro-brush.

The brush section has a diameter of between about 0.2 mm and about 2 mm at its tip end and a diameter of between about 0.5 mm and 3 mm at its coronal end. The brush section is about 16 mm long, and has a taper of between about 2% and about 12%. The core which retains the bristles can have a constant taper, an increasing progressive taper, or a decreasing progressive taper to achieve the correct diameter, flexibility and rigidity. The length of the bristles changes over the length of the brush. Specifically, the bristles may be as short as 0.05 mm towards the distal or tip end of the brush and 3 mm towards the most proximal or coronal end of the brush.

Importantly, the entire brush is formed in an injection molding process and is manufactured from a resin, such as plastic. This process generates a brush core, the distal end of which is 0.1 mm in diameter, or four times smaller than the combined diameter of the two braided wires used to retain bristles as described in my prior patent, Pat. No. 6,179,617. With the bristles mounted to the plastic core, the brush will have a diameter which will allow it to reach the end of the root canal.

Brushes are also provided for cleaning the root canal access cavity and pulp chamber, which, as is known, provides access to the orifices of the root canals. These brushes have a handle, a shank and a brush section extending from the shank. The brush section includes bristles extending from a central core. The core can be spherical, football shaped, or tapered. The spherical brushes have a spherical core which have diameters between about 0.5 mm and about 2 mm and the bristles have a length of from about 0.5 mm to about 3 mm. The football shaped cores have diameters ranging from between about 0.5 mm and about 3 mm at their widest central sections and have diameters of between about 0.25 mm and 1 mm at their opposing ends. The bristles have lengths between about 0.05 mm and about 3 mm. Lastly, the tapered cores have lengths between about 5 mm and 15 mm. Each core has a side surface and an end surface, and the bristles extend from the core side and end surfaces. The tapered cores have diameters from about 0.5 mm to about 2 mm at their tips and from about 1 mm to about 3 mm at their coronal ends. The taper of the cores is between about 2% and about 12%.

DETAILED DESCRIPTION OF THE INVENTION

Figure 1:
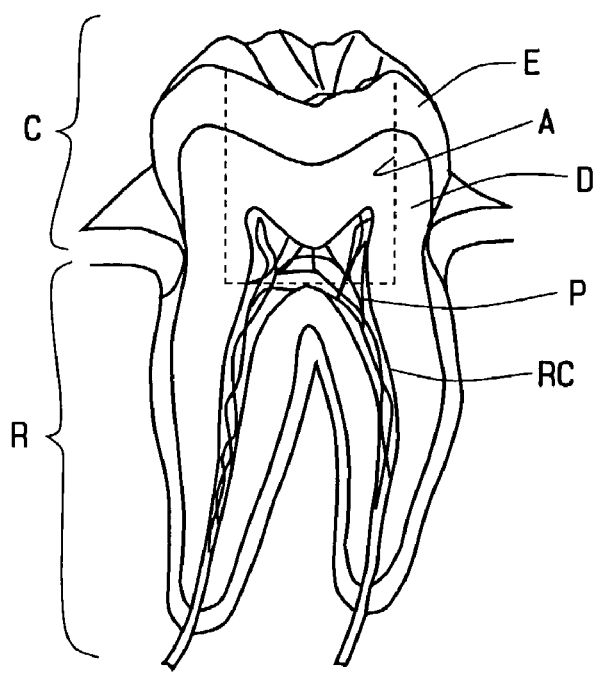
FIG. 1 is a cross-sectional view showing the anatomy of a tooth.

The following detailed description illustrates the invention by way of example and not by way of limitation. This description will clearly enable one skilled in the art to make and use the invention, and describes several embodiments, adaptations, variations, alternatives and uses of the invention, including what I presently believe is the best mode of carrying out the invention. Additionally, it is to be understood that the invention is not limited in its application to the details of construction and the arrangements of components set forth in the following description or illustrated in the drawings. The invention is capable of other embodiments and of being practiced or being carried out in various ways. Also, it is to be understood that the phraseology and terminology used herein is for the purpose of description and should not be regarded as limiting.

A tooth T is shown in FIG. 1. As is known, a tooth includes a crown C and a root R. The crown and root are comprised primarily of dentin D. The dentin of the crown is covered with enamel E. At the base of the crown, the tooth T includes a pulp chamber P from which root canals RC extend. The root canals RC extend to the terminus of the roots R. In healthy teeth, the pulp chamber P and root canals RC are filled with pulp tissue. As is known, when the pulp tissue becomes irreversibly inflamed, partially infected or completely abscessed, it is necessary to clean out, disinfect, and fill the pulp chamber and root canal with a biologically compatible filling material. To do this, an access cavity A (shown in dotted lines in FIG. 1) is formed in the crown C. The access cavity A is sized, as is known, to allow a practitioner to access the orifices of the root canals. The typical procedure for preparing the access cavity is described above.

Figure 2D:
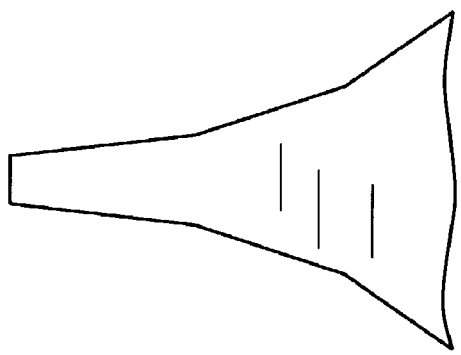
FIGS. 2D and 2E are schematic drawings of increasing and decreasing progressive tapers for the brush.
Figure 2E:
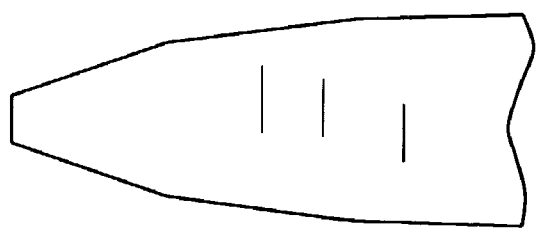
Figure 2A:
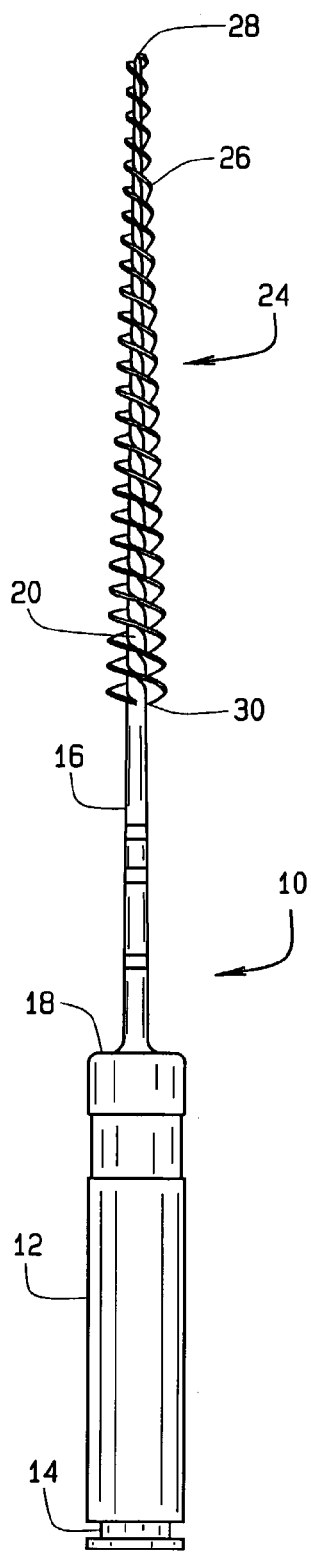
FIGS. 2A–C are side elevational views of a first embodiment of a canal brush of the present invention, showing the brush in three different sizes.
Figure 2B:
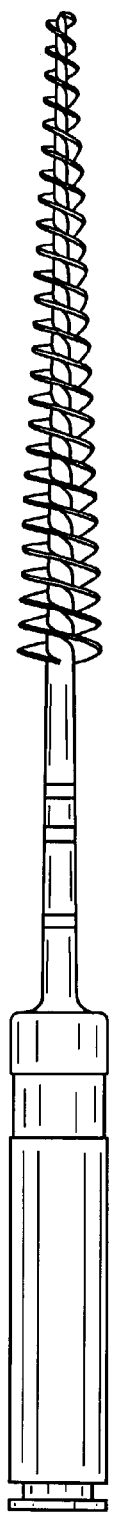
Figure 2C:
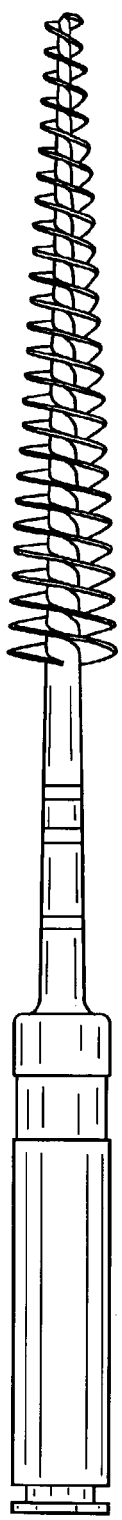
Figure 3:
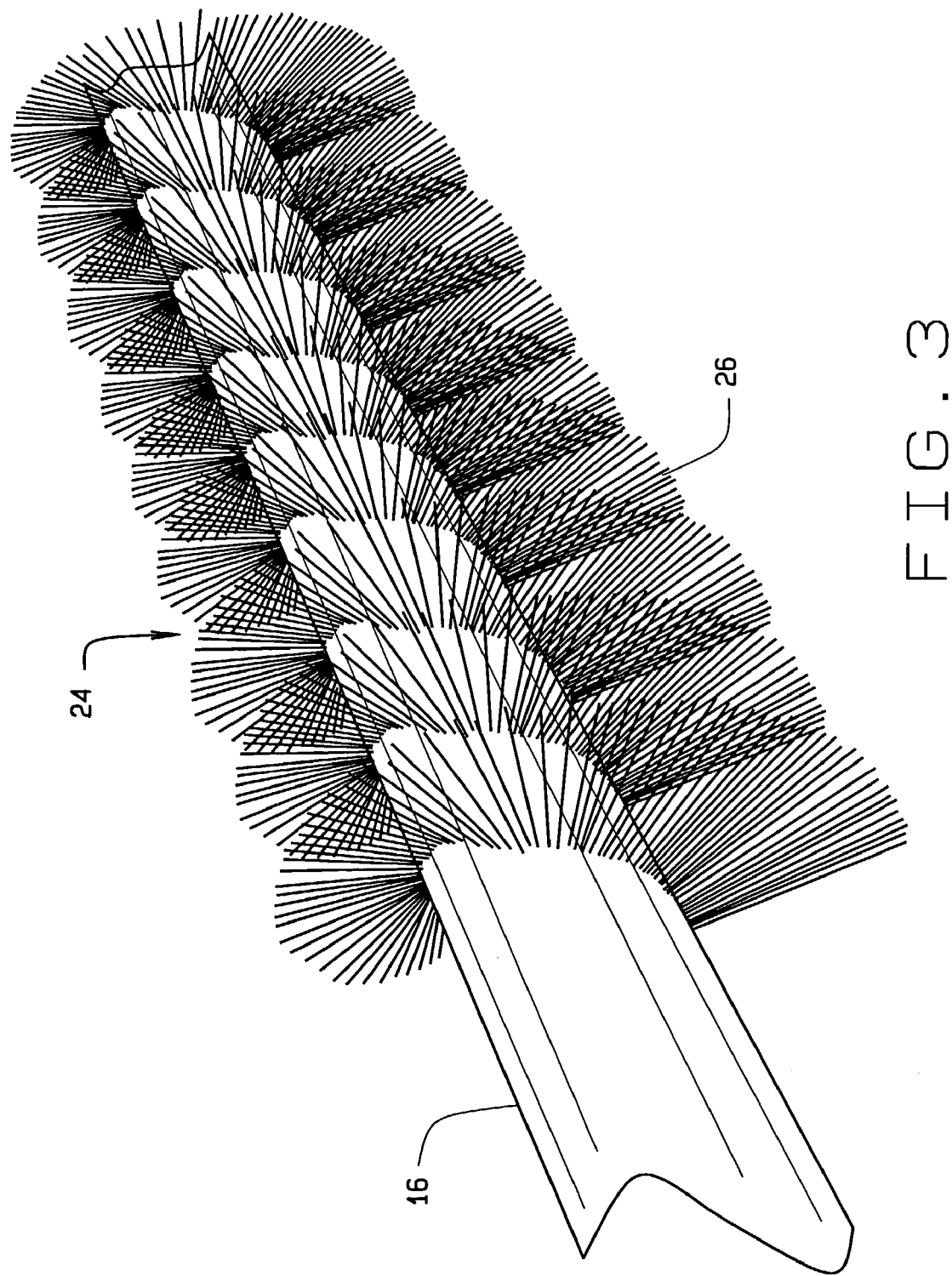
FIG. 3 is an enlarged view of the brush section of the brush of FIGS. 2A–C.

A canal brush 10 of the present invention is shown in FIGS. 2A–C. The brushes shown in FIGS. 2A–C are substantially similar in appearance. The difference between the brushes is that FIG. 2A shows a small canal brush; FIG. 2B shows an intermediate canal brush; and FIG. 2C shows a large canal brush. The three different brushes can be used by a practitioner for different sized canals (i.e., use the small brush for small canals and the large brush for large canals). Alternatively, the practitioner can use the different size brushes to clean different areas of a canal, as the canal changes in size from its coronal end to the end of the root R.

The canal brush 10 includes a handle 12 which is adapted at its end 14 for connection to a rotary tool, an ultrasonic handpiece, or another instrument which can rotate or vibrate the brush. Alternatively, the handle 12 can be shaped and sized to be held by the practitioner.

A shank 16 extends from the end 18 of the handle 12, and a brush 24 extends from the end of the shank 16. The brush 24 includes a core 20 from which a plurality of bristles 26 extend. The shank 16 is a continuation of the core 20 and spaces the bristles from the handle end 18. The bristles 26 extend radially from the core 20 and preferably are formed in a helical or spiral pattern. More preferably, the bristles 26 define a helical pattern so that as the brush is rotated in a root canal, the bristles will, in effect, auger material up and out of the root canal. The bristles 26 are made from a synthetic material which is sufficiently stiff so that it will have good rubbing action against the root canal wall to remove the smear layer, which is sufficiently pliable so that the bristles can bend and flex to reach the normal irregularities in the root canal wall, and which is sufficiently soft so that the use of the brush will not form gouges or ledges in the root canal wall (i.e., will not substantially change the normal morphology of the root canal system).

The handle 12, shank 16, and core 20 are preferably formed in an injection molding process to form a single, unitary, one-piece, integrally formed unit. The handle, shank, and core are preferably molded from the same material, however, they can be co-molded from different resins if desired. The core 20 is preferably tapered, as seen in FIGS. 2A–2C. The core has a diameter of between 0.1 mm and 2 mm at the tip or distal end 28 of the brush. At the coronal end 30, the core has a diameter of between about 0.5 mm and about 3 mm. As can be appreciated, the small brush will have the smallest diameters, the large brush will have the larger diameters, and the medium brush will have diameters between the small and large brushes. Preferably, the taper is between about 2% and about 12%.

The core 20 is made from an FDA medically approved resin material which, when set, will allow the core to be sufficiently flexible to bend around curves in the root canals RC, and yet will be sufficiently rigid so that the practitioner can use the brush to effectively remove the smear layer from the surfaces of the root canal RC. Preferably, the resin will provide a core 20 having a flexibility comparable to the flexibility of between a #15 and a #40 stainless steel ISO K-type file. To obtain the appropriate balance between rigidity and flexibility, the core 24 may change diameter over its length. The core 24 can have a constant or fixed taper or a taper which progressively changes over its length. If the core has a progressive taper, the progressive taper can be either an increasing progressive taper or a decreasing progressive taper. The brushes shown in FIGS. 2A–C all have cores with a constant taper. FIG. 2D shows a core with an increasing progressive taper; and FIG. 2E shows a core with a decreasing progressive taper.

The bristles have a length of about 0.05 mm to about 2 mm, such that the overall diameter of the brush 24 (when the core diameter and bristle length are added together) is about 0.2 mm to about 2 mm at the tip 28 of the brush and is about 0.5 mm to about 3 mm at the coronal end 30 of the brush. The brush 24 is about 16 mm long, and has a taper of between about 2% to about 12% and preferably between 4% to about 10%

Figures 4A, 4B, 4C:
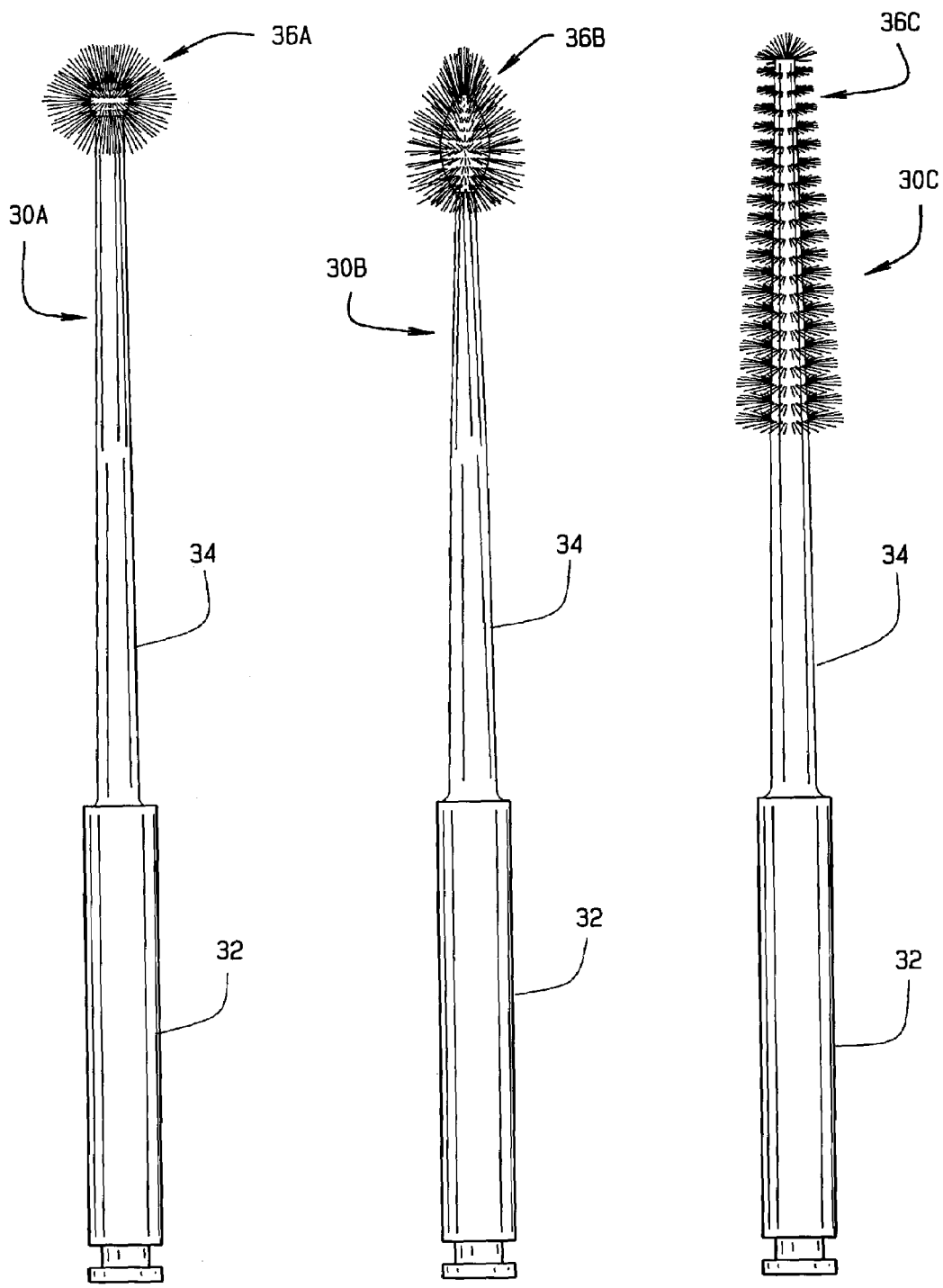
FIGS. 4A–C are side elevational views of three different canal access chamber brushes.

The canal brushes of FIGS. 2A–C are sized, as noted, to be used in the root canal. However, part of the endodontic procedure includes cleaning the smear layer from the access cavity A (FIG. 1). The canal brushes are too small to be used to effectively clean the access cavity A. The chamber brushes 30A–C of FIGS. 4A–C are sized to be used within the access cavity A. Like the brushes 10 of FIGS. 2A–C, the brushes 30A–C all have a handle 32, a shank 34, and a brush 36A–C at the end of the shank 34. The handle 32 is adapted to be used manually or to be connected to a rotary handpiece, an ultrasonic handpiece, or another device which can rotate or vibrate the brush. The brushes 36A–C each comprise a core 38A–C from which bristles 40 extend. The handle 32, shank 34 and core 38A–C are preferably injection molded to form a one-piece unitary part from a suitable FDA medically approved resin. The bristles 40 are embedded (or otherwise secured) in the core during the injection molding process. As with the brushes 10, the handle, shank and core of the brushes 30A–C can be formed from the same resin, or can be co-molded from different resins. If the handle, shank, and core are formed from two, three, or more different resins, the unit may be molded in a multiple-injection process. However, whether formed in a single-injection molding process or a multiple-injection molding process, the handle, shank, and core form a one-piece unitary part. Also, as with the canal brushes 10, the chamber brushes 36A–C can be provided in varying sizes for use with teeth having different sized access cavities. For example molars will have access cavities far greater in size than the access cavities prepared in mandibular anterior teeth.

Figure 5C:
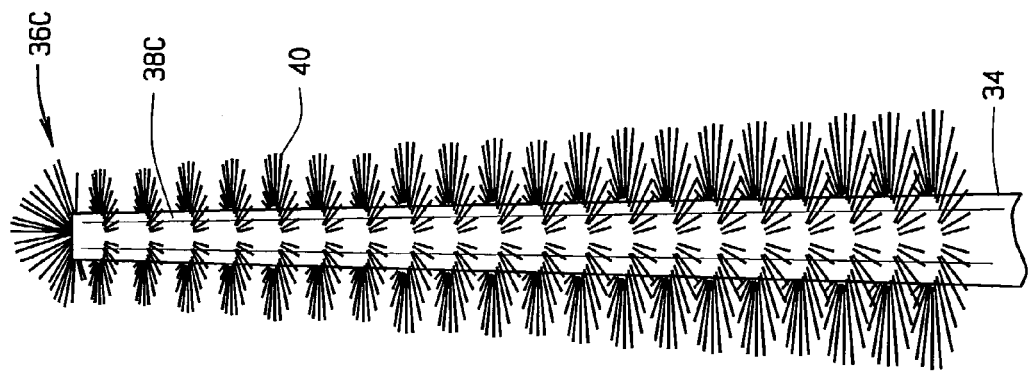
FIGS. 5A–C are enlarged views of the heads or brush sections of the brushes of FIGS. 4A–C, respectively Corresponding reference numerals will be used throughout the several figures of the drawings.
Figure 5B:
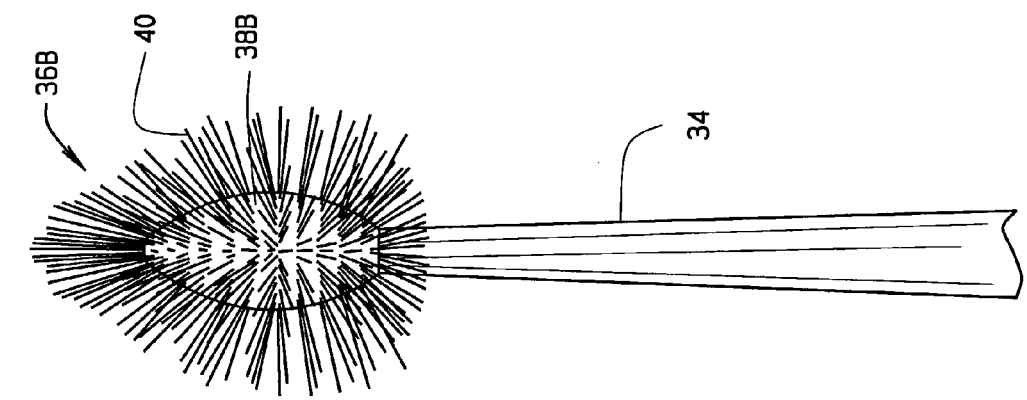
Figure 5A:
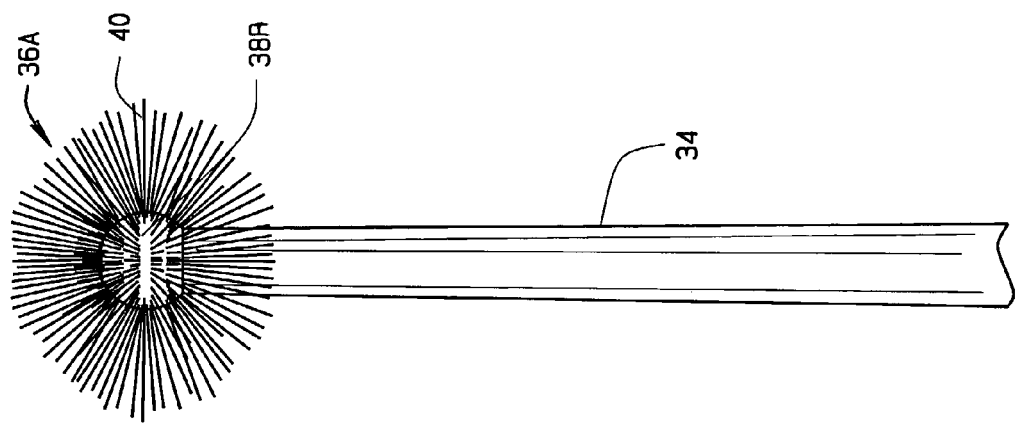

As best seen in FIGS. 5A–C, the core 38A of the brush 30A is formed to be generally spherical, and the bristles 40 radiate from all around the spherical core to form a brush section which is generally spherical. The core 38A can have diameters of between about 0.5 mm and about 2 mm; and the bristles have a length of about 0.25 mm to about 3 mm. Thus, the spherical brush section 36A has a diameter of about 1 mm to about 5 mm.

The core 38B of the brush 30B has a generally football or oval shape. The core 38B has a length from end to end of about 3 mm to about 5 mm, and a diameter of about 0.5 mm to about 2 mm at its widest point, which is preferably about mid-way between the two opposing ends of the core, a diameter of between about 0.25 mm and 1 mm at its opposing ends. The bristles 40 extend from all around the core to form a brush section which is generally football shaped. The bristles have a length of about 0.5 mm to about 3 mm. Thus, the football shaped brush section 36B has a length of about 3.5 mm to about 8 mm (including both the core and the bristle length) and diameter at its midpoint (and widest point) of about 1.5 mm to about 5 mm (including both the core diameter and the bristle length).

The core 38C of the brush 30C is formed to be generally conical. The core 38C thus has a taper, which is preferably constant. The core is preferably about 10 mm long, and has a diameter of about 0.5 mm to about 2 mm at its tip end and a diameter of about 1.0 to about 3.0 at its back end, where the core joins the shank. Preferably, as seen, there is a smooth transition between the shank 34 and the core 38C. The bristles 40 radiate from the side and end surface of the core 38C. The bristles have a length of about 0.5 mm to about 3 mm. Thus, the conical brush section 36C has an overall length of about 11 mm to about 14 mm; an overall diameter of about 1–2 mm at its tip end and a diameter of about 4–6 mm at its back end. Thus, the brush has a taper or slope of about 2% to about 12%.

As various changes could be made in the above constructions without departing from the scope of the invention, it is intended that all matter contained in the above description or shown in the accompanying drawings shall be interpreted as illustrative and not in a limiting sense.

What is claimed is:

1. A one-piece, integrally formed microbrush for use in cleaning a root canal during an endodontic procedure on a living patient after the root canal has been shaped but before obturation of the root canal system:
   a handle adapted to be connected to a dental handpiece or hand-held by a practitioner for inserting the microbrush through an access cavity preparation in the tooth, through an orifice into the root canal; and a brush section operatively connected to and extending from said handle; said brush section comprising a core and a plurality of bristles projecting outwardly from the core to clean debris and other material out of the root canal as the core is inserted therethrough, in preparation for filling the root canal; said core being molded from a plastic resin; said microbrush having an overall diameter, at least at a distal end, sized to enable the microbrush to reach the apical ends of root canals; said brush section being tapered and having a first diameter at a tip end of said brush section and a second, larger, diameter at the coronal end of said brush section; said taper being a progressive taper.

2. The microbrush of claim 1 including a shank extending from the handle; the core extending from the end of the shank; said core and shank being molded as a unitary, one-piece part from said resin.

3. The microbrush of claim 1 wherein the taper is an increasing progressive taper.

4. The microbrush of claim 1 wherein the taper is a decreasing progressive taper.

5. The microbrush of claim 1 wherein said core has a diameter of between about 0.1 mm and about 2 mm at the tip end of the brush section and a diameter of between about 0.5 mm and about 3 mm at the coronal end of the brush section.

6. The microbrush of claim 5 wherein the bristles have a length of about 0.05 mm to about 2 mm.

7. The microbrush of claim 5 wherein the core has a taper of between about 2% and about 12%.

8. The microbrush of claim 1 in which the bristles are formed in a helical pattern along a length of the core.

9. The microbrush of claim 8 wherein the bristles define a reverse helical pattern such that, as said brush is rotated within a canal, debris will be removed from the canal.

10. The microbrush of claim 1 wherein said core has a diameter of about 0.1 mm at the tip end of the brush section and the bristles have a length of about 0.05 mm, such that the brush has an overall diameter of about 0.2 mm at the tip end of the brush.

11. The microbrush of claim 1 wherein the core has a flexibility comparable to the flexibility of between an #15 and a #40 stainless steel ISO K-type file.

12. A one-piece, integrally formed brush for use in cleaning a root canal access cavity during an endodontic procedure on a living patient after the root canal and cavity have been shaped but before obtu ration; the brush having a handle and a tapered brush section; the brush section including a central core operatively connected to the handle and a plurality of bristles radiating from the central core, said bristles extending to an apical end of said core and covering the apical end of said core; said handle and core being integrally formed together from a resin as a one-piece part; said brush having an overall diameter, at a distal end of about 0.2 mm, such that the distal end of the brush is sized to enable the brush to reach the apical ends of root canals.

13. The brush of claim 12 wherein said core has a diameter of about 0.5 mm to about 2 mm at its widest section and said bristles have a length of about 0.5 mm to about 3 mm.

14. The brush of claim 12 wherein said core is a tapered core having a side surface and an end surface; said bristles extending from the core side and end surface.

15. The brush of claim 14 wherein said tapered core has a diameter of about 1 mm to about 3 mm at its coronal end; and a taper of about 2% to about 12%.

16. A one-piece, integrally formed endodontic instrument for use in cleaning a root canal during an endodontic procedure on a living patient after the root canal has been shaped but before obtu ration of the root canal system; the instrument comprising a handle, a tapered core, and a plurality of bristles extending from a lower section of said core to define a brush portion of said instrument; said bristles being sufficiently stiff so that they will have good rubbing action against a root canal wall to remove a smear layer from the root canal wall, sufficiently pliable so that the bristles can bend and flex to reach the normal irregularities in the root canal wall, and sufficiently soft so that the use of the brush portion will not form gouges or ledges in the root canal wall;

said handle being adapted to be connected to a dental handpiece or hand-held by a practitioner for inserting the instrument core through an access cavity preparation in the tooth, through an orifice at the start of the root canal, and into the root canal;

said core being molded from a resin; said bristles having a length, such that at the distal end of said brush portion, said brush portion has an overall diameter at its distal end of about 0.2 mm, whereby said endodontic instrument is sized to enable the brush portion to reach the apical ends of root canals.

17. The endodontic instrument of claim 16 wherein said bristles have a length of about 0.05 mm and said core has a diameter of about 0.1 mm.

* * * * *